(12) United States Patent
Busacca et al.

(10) Patent No.: US 7,309,700 B2
(45) Date of Patent: Dec. 18, 2007

(54) CRYSTALLINE FORMS OF 5,11-DIHYDRO-11-ETHYL-5-METHYL-8-{2-{(1-OXIDO-4-QUINOLINYL)OXY}ETHYL}-6H-DIPYRIDO[3,2-B:2',3'-E][1,4]DIAZEPIN-6-ONE

(75) Inventors: Carl A. Busacca, Poughkeepsie, NY (US); Michael Cerreta, Newtown, CT (US); Richard Varsolona, Scotch Plains, NJ (US); John Smoliga, Brookfield, CT (US); Jon Lorenz, New Milford, CT (US); Jana Vitous, Danbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 110 days.

(21) Appl. No.: 11/083,401

(22) Filed: Mar. 18, 2005

(65) Prior Publication Data

US 2005/0222134 A1    Oct. 6, 2005

Related U.S. Application Data

(60) Provisional application No. 60/559,354, filed on Apr. 2, 2004.

(51) Int. Cl.
*C07D 471/14* (2006.01)
*A61K 31/55* (2006.01)

(52) U.S. Cl. ...................................................... 514/220
(58) Field of Classification Search ................ 540/495; 514/220
See application file for complete search history.

(56) References Cited

U.S. PATENT DOCUMENTS 6,420,359 B1   7/2002   Simoneau
6,759,533 B2   7/2004   Busacca et al.

FOREIGN PATENT DOCUMENTS

WO        0196338      12/2001
WO        2004002989   1/2004

OTHER PUBLICATIONS

Brittain, et al; "Polymorphism in Pharmaceutical Solids Passage"; Drug and Pharmaceutical Sciences, 1999, vol. 95, pp. 235-238.
Caira, M. R.; "Crystalline Polymorphism of Organic Compounds"; Topics in Current Chemistry; Springer, Berlin, Germany, 1999, vol. 198, pp. 163-208.

*Primary Examiner*—Bruck Kifle
(74) *Attorney, Agent, or Firm*—Michael P. Morris; Mary-Ellen M. Devlin; Alan R. Stempel

(57) ABSTRACT

Dihydrate and anhydrous crystalline forms of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one.

8 Claims, 5 Drawing Sheets

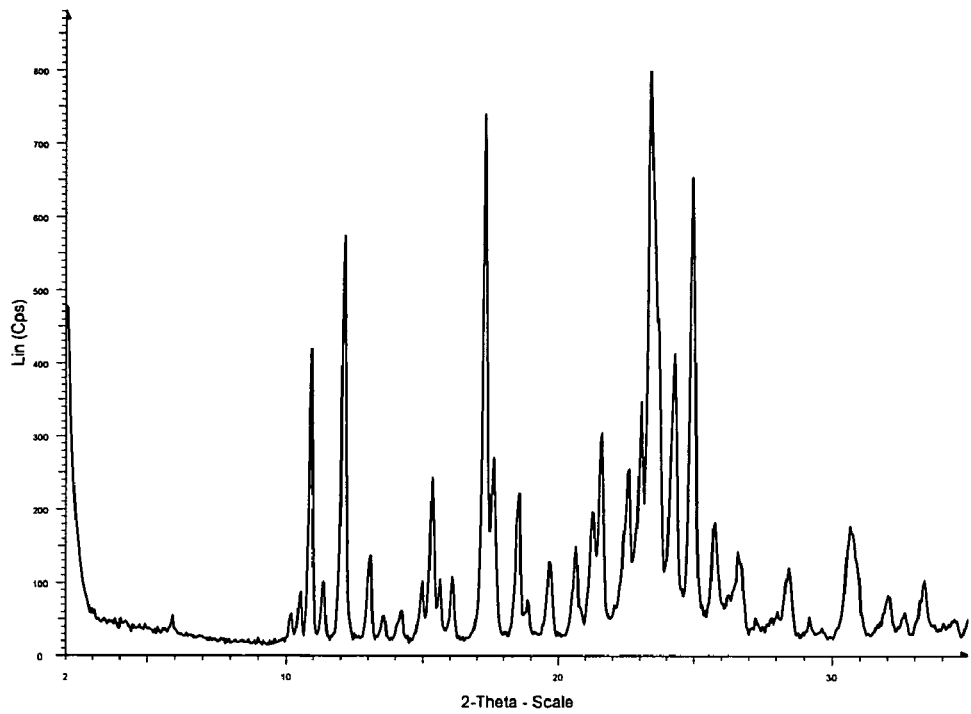
Figure 1. XRPD Pattern of 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate. Data collected using Cu kα radiation.

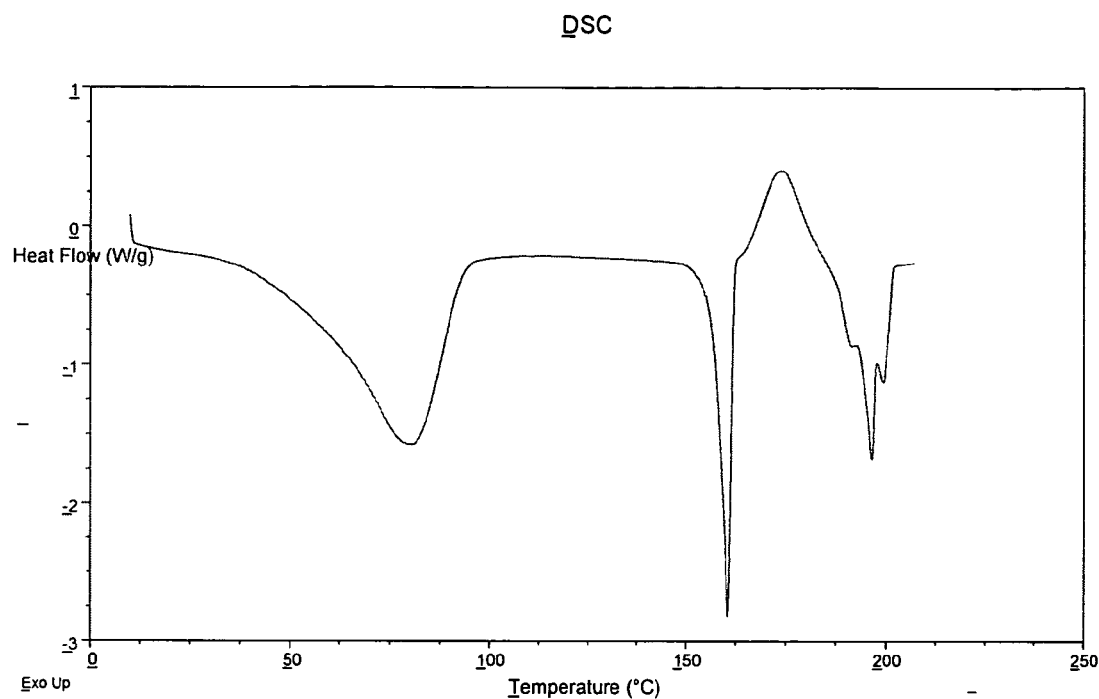
Figure 2. DSC Thermal Curve of 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate.

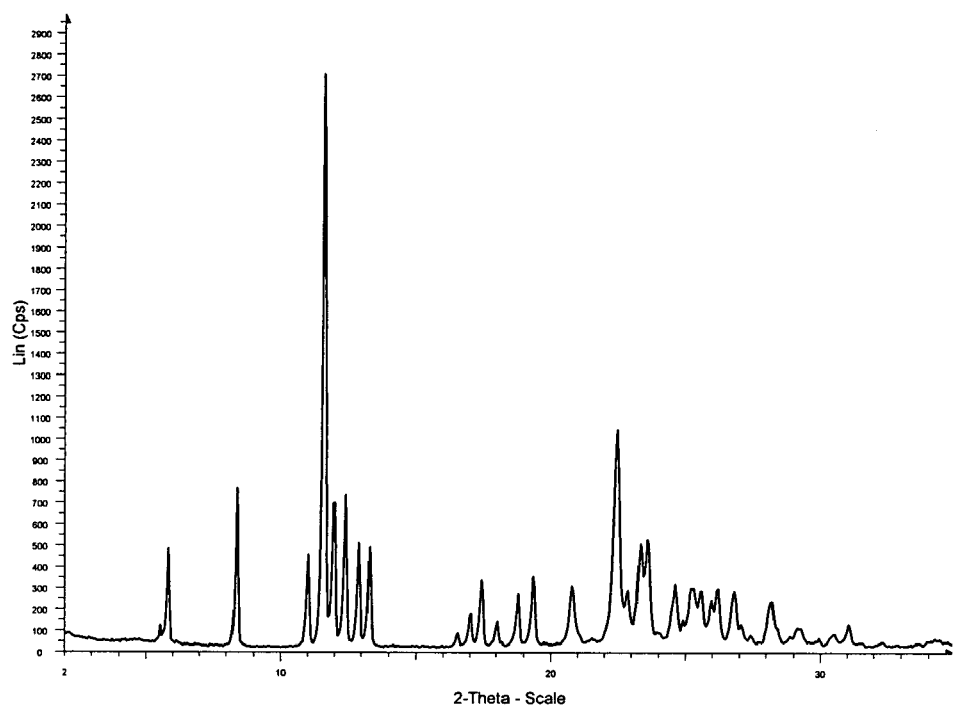
Figure 3. XRPD Pattern of 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one Anhydrous Form III. Data collected using Cu kα radiation.

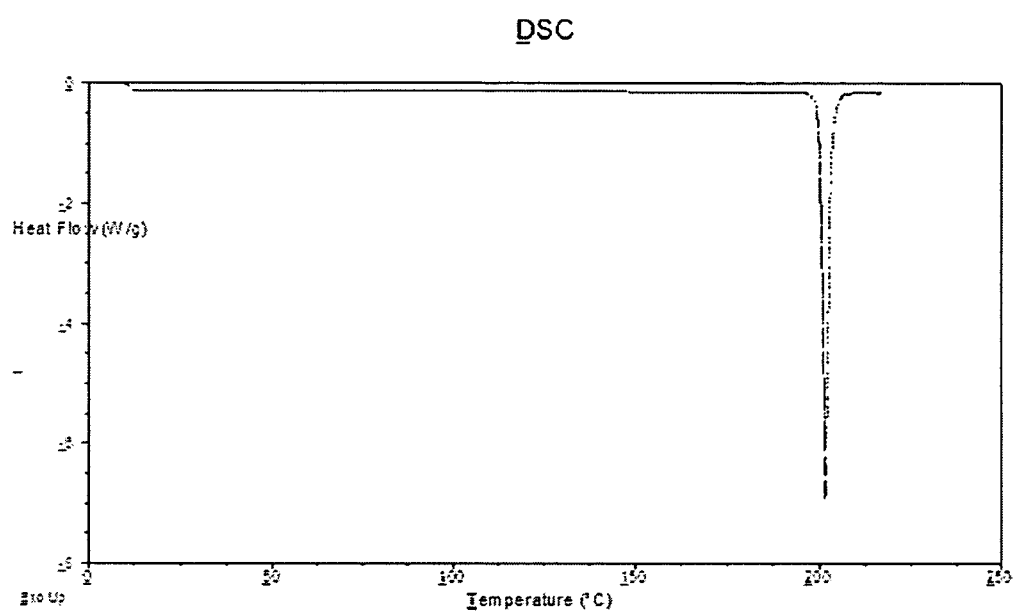
Figure 4. DSC Thermal Curve of 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one Anhydrous Form III.

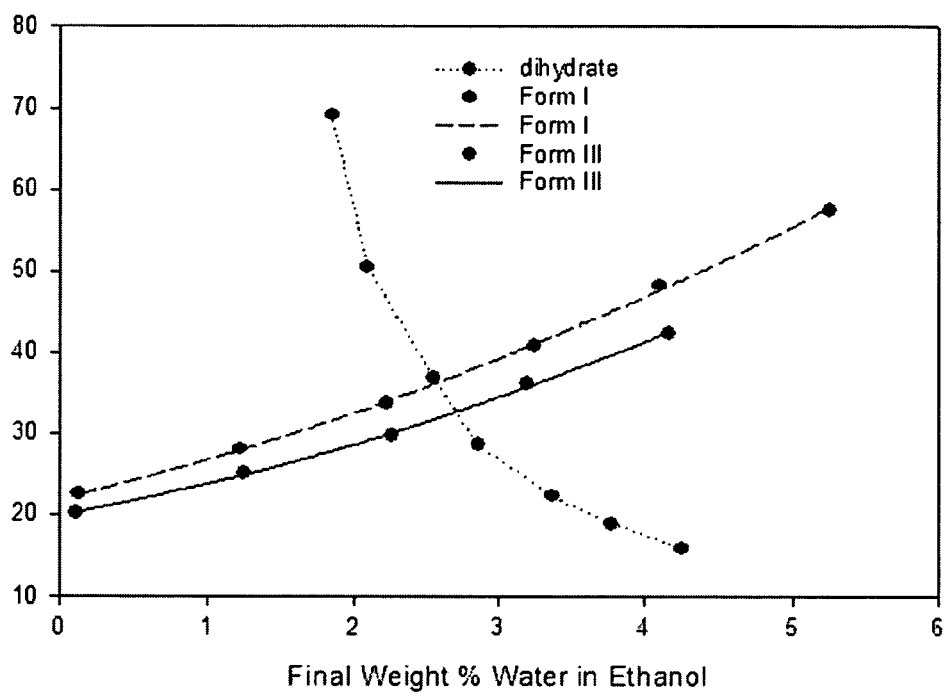
Figure 5. Phase Diagram of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one.

CRYSTALLINE FORMS OF 5,11-DIHYDRO-11-ETHYL-5-METHYL-8-{2-{(1-OXIDO-4-QUINOLINYL)OXY}ETHYL}-6H-DIPYRIDO[3,2-B:2',3'-E][1,4]DIAZEPIN-6-ONE

CROSS-REFERENCE TO RELATED APPLICATIONS

Benefit of Provisional Application 60/559,354 filed on Apr. 2, 2004 is hereby claimed.

BACKGROUND OF THE INVENTION

1. Technical Field

The present invention relates to dihydrate and anhydrous crystalline forms of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one.

2. Background Information 5,11-Dihydro-11-ethyl-5-methyl-8-{2-{(1-oxido-4-quinolinyl)oxy}ethyl}-6H-dipyrido[3,2-b:2',3'-e][1,4]diazepin-6-one is a non-nucleoside HIV-1 reverse transcriptase inhibitor. Its chemical structure is as depicted below.

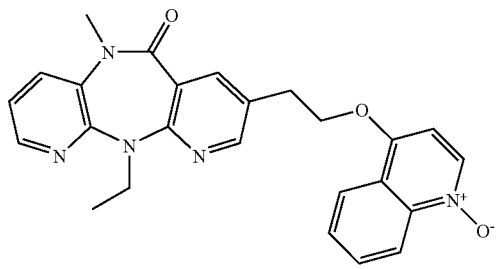

The synthesis of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one, its use for the treatment of HIV infection, and pharmaceutical compositions comprising this substance and suitable for this use are described in U.S. Pat. No. 6,420,359 and the corresponding WO0196338.

BRIEF SUMMARY OF THE INVENTION

We have discovered that when 5,11-dihydro-11-ethyl-5-methyl-8-{2-{(1-oxido-4-quinolinyl)oxy}ethyl}-6H-dipyrido[3,2-b:2',3'-e][1,4]diazepin-6-one is made in the manner described in U.S. Pat. No. 6,420,359 and the corresponding WO0196338 the resulting material is a poorly crystalline trihydrate. We have further discovered that the trihydrate is not the most desirable form of this drug substance to be used in the development of a drug product.

A first aspect of the present invention comprises the discovery of a dihydrate crystalline form of 5,11-dihydro-11-ethyl-5-methyl-8-{2-{(1-oxido-4-quinolinyl)oxy}-ethyl}-6H-dipyrido[3,2-b:2',3'-e][1,4]diazepin-6-one. This dihydrate crystalline form is thermodynamically or kinetically favored at temperatures and humidity's that are most likely to be encountered upon storage of drug substance or drug product and thus pharmaceutically preferred to the trihydrate that is provided by the prior art. The invention also comprises methods for making this dihydrate crystalline form.

We have further discovered that under proper conditions several anhydrous polymorphs of 5,11-dihydro-11-ethyl-5-methyl-8-{2-{(1-oxido-4-quinolinyl)oxy} ethyl}-6H-dipyrido[3,2-b:2',3'-e][1,4]diazepin-6-one may be formed. One of these, which we designate as anhydrous Form III (AF III), has demonstrated phase stability at some tested ambient conditions, which indicates that it is pharmaceutically acceptable, and biological testing has shown that it leads to higher plasma levels than are attainable using other crystalline forms of the drug. Thus, the invention further includes anhydrous Form III of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one and methods for its manufacture.

BRIEF DESCRIPTION OF THE DRAWINGS

FIG. 1 is an XRPD Pattern of 5,11-Dihydro-11-ethyl-5-methyl-8-{2-{(1-oxido-4-quinolinyl)oxy}ethyl}-6H-dipyrido[3,2-b:2',3'-e][1,4]diazepin-6-one dihydrate.

FIG. 2 is a DSC Thermal Curve of 5,11-Dihydro-11-ethyl-5-methyl-8-{2-{(1-oxido-4-quinolinyl) oxy}ethyl}-6H-dipyrido[3,2-b:2',3'-e][1,4]diazepin-6-one dihydrate.

FIG. 3 is an XRPD Pattern of 5,11-Dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III.

FIG. 4 is a DSC Thermal Curve of 5,11-Dihydro-11-ethyl-5-methyl-8-{2-{(1-oxido-4-quinolinyl) oxy}ethyl}-6H-dipyrido[3,2-b:2',3'-e][1,4]diazepin-6-one Anhydrous Form III.

FIG. 5 is a Phase Diagram of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one.

DETAILED DESCRIPTION OF THE INVENTION

1. Identification by Characteristic X-ray Powder Diffraction Patterns

As noted previously, the invention comprises two novel crystalline forms of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one, the dihydrate and anhydrous Form III. These may be identified and distinguished from each other and from other crystalline forms that are not part of the invention by means of their characteristic X-ray Powder Diffraction (XRPD) patterns.

The dihydrate crystalline form of 5,11-dihydro-11-ethyl-5-methyl-8-{2-{(1-oxido-4-quinolinyl oxy}ethyl}-6H-dipyrido[3,2-b:2',3'-e][1,4]diazepin-6-one that is in accordance with the invention is characterized by having an X-ray powder diffraction pattern that comprises a peak at 23.4 degrees 2θ (±0.2 degrees 2θ), wherein said X-ray powder diffraction pattern is made using CuK$_\alpha$ radiation.

Preferably, the dihydrate in accordance with the invention is characterized by having an X-ray powder diffraction pattern that comprises peaks at 23.4 and 24.9 degrees 2θ (±0.2 degrees 2θ) and wherein said X-ray powder diffraction pattern is made using CuK$_\alpha$ radiation.

More preferably, the dihydrate in accordance with the invention is characterized by having an X-ray powder diffraction pattern that comprises peaks at 23.4, 24.9 and 17.3, degrees 2θ (±0.2 degrees 2θ) and wherein said X-ray powder diffraction pattern is made using CuK$_\alpha$ radiation.

Still more preferably, the dihydrate in accordance with the invention is characterized by having an X-ray powder diffraction pattern that comprises peaks at 23.4, 24.9, 17.3, 24.3, 12.1, 18.5 and 17.6 degrees 2θ (±0.2 degrees 2θ) and wherein said X-ray powder diffraction pattern is made using CuK$_\alpha$ radiation.

More specifically, the dihydrate in accordance with the invention is characterized by having an X-ray powder diffraction pattern, made using CuK$_\alpha$ radiation, which is substantially the same as that shown in FIG. 1.

The anhydrous Form III crystalline form of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one that is in accordance with the invention is characterized by having an X-ray powder diffraction pattern that comprises a peak at 11.6 degrees 2θ (±0.2 degrees 2θ), wherein said X-ray powder diffraction pattern is made using CuK$_\alpha$ radiation.

Preferably, the anhydrous Form III crystalline form in accordance with the invention is characterized by having an X-ray powder diffraction pattern that comprises peaks at 11.6, 22.5 and 8.3 degrees 2θ (±0.2 degrees 2θ), wherein said X-ray powder diffraction pattern is made using CuK$_\alpha$ radiation.

More preferably, the anhydrous Form III crystalline form in accordance with the invention is characterized by having an X-ray powder diffraction pattern that comprises peaks at 11.6, 22.5, 8.3, 12.0, 12.4 and 5.8 degrees 2θ (±0.2 degrees 2θ), wherein said X-ray powder diffraction pattern is made using CuK$_\alpha$ radiation.

Still more preferably, the anhydrous Form III crystalline form in accordance with the invention is characterized by having an X-ray powder diffraction pattern that comprises peaks at 11.6, 22.5, 8.3, 12.0, 12.4, 5.8, and 20.8 degrees 2θ (±0.2 degrees 2θ), wherein said X-ray powder diffraction pattern is made using CuK$_\alpha$ radiation.

More specifically, the anhydrous Form III crystalline form in accordance with the invention is characterized by having an X-ray powder diffraction pattern, made using CuK$_\alpha$ radiation, which is substantially the same as that shown in FIG. 3.

In order to allow for experimental error, the above described 2θ values should be considered accurate to ±0.2 degrees 2θ. That is to say, when assessing whether a given sample of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one is the dihydrate or anhydrous Form III crystalline form in accordance with the invention, a 2θ value which is experimentally observed for the sample should be considered identical with a characteristic value described above if it falls within ±0.2 degrees 2θ of the characteristic value.

The crystalline forms in accordance with the invention are preferably employed as drug active substances in substantially pure form, that is to say, essentially free of other crystalline forms 5,11-dihydro-11-ethyl-5-methyl-8-{2-{(1-oxido-4-quinolinyl)oxy}ethyl}-6H-dipyrido[3,2-b:2',3'-e][1,4]diazepin-6-one. Nevertheless, the invention also embraces the dihydrate crystalline form or the anhydrous Form III crystalline form in admixture with another crystalline form or forms. Should the drug active substance be a mixture of crystalline forms, it is preferred that the substance comprise at least 50% of either the dihydrate or anhydrous form III crystalline form described herein.

2. Synthesis

The invention further provides processes for the synthesis of the dihydrate and anhydrous Form III of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one.

(A) General Synthetic Methods According to the Invention (i) General Synthetic Method for the production of the dihydrate crystalline form of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one In most general terms, the dihydrate crystalline form is prepared by recrystallinzing 5,11-dihydro-11-ethyl-5-methyl-8-{2-{(1-oxido-4-quinolinyl)oxy}ethyl}-6H-dipyrido[3,2-b:2',3'-e][1,4]diazepin-6-one in crude form, prepared by any synthetic method (including but not limited to that described in U.S. Pat. No. 6,420,359 or the corresponding WO0196338), from water. This is accomplished by suspending 5,11-dihydro-11-ethyl-5-methyl-8-{2-{(1-oxido-4-quinolinyl)oxy}ethyl}-6H-dipyrido[3,2-b:2',3'-e][1,4]diazepin-6-one in a mixture of water and a solvent which is both water-miscible and a liquid near ambient temperature. Suitable solvents include the lower alkylnitriles (for example acetonitrile and propionitrile), lower alkyl alcohols (C1-C7, for example methanol, ethanol, and isopropanol), cyclic and acyclic ethers including polyethers (for example tetrahydrofuran, dioxane and diglyme), amides (for example dimethylformamide, N-methylpyrrolidinone and dimethylacetamide), sulfoxides (for example DMSO), sulfones (for example sulfolane), lower alkylketones (for example acetone), and lower alkyl nitroalkanes (for example nitromethane). The suspension is heated until a clear solution that is saturated or nearly saturated is obtained. The amount of water must be at least that required to form a stoichiometric dihydrate with the amount of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one used, and less than about 90% of the overall solvent mixture. If a solution is not obtained, additional volumes of solvent are then added at elevated temperature until a clear solution is formed. The solution is then allowed to cool slowly to a lower temperature, until a crystalline precipitate is first observed. The slurry is then held at that temperature until precipitation has essentially ceased. The precipitate is then removed from solution, for example by filtration. The solid is then dried until all surface solvents have been removed, providing 5,11-dihydro-11-ethyl-5-methyl-8-{2-{(1-oxido-4-quinolinyl)oxy}ethyl}-6H-dipyrido[3,2-b:2',3'-e][1,4]diazepin-6-one dihydrate.

(ii) General Synthetic Method for the production of Anhydrous Form III of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one 5,11-Dihydro-11-ethyl-5-methyl-8-{2-{(1-oxido-4-quinolinyl)oxy}ethyl}-6H-dipyrido[3,2-b:2',3'-e][1,4]diazepin-6-one dihydrate or trihydrate (produced by any method) is dried to remove H$_2$O. This drying can be performed by any means, such as drying in an oven at 23° C. or higher temperature and at atmospheric pressure or under vacuum. It may be dried by vigorous passage of a dry, inert gas over the solid for extended periods, or it may be chemically dried, for example by distillation to remove water with any solvent which can form an azeotropic mixture with water. Exemplary solvents are lower alkylnitriles (such as acetonitrile), lower alkylalcohols (such as ethanol and isopropanol) and ethers (such as dioxane and THF). Drying is performed until analysis shows that <1% water remains. This dry solid is then dissolved in an anhydrous solvent in which 5,11-dihydro-11-ethyl-5-methyl-8-

{2-{(1-oxido-4-quinolinyl)oxy}ethyl}6H-dipyrido[3,2-b:2',3'-e][1,4]diazepin-6-one is soluble (such as, for example, ethanol), at elevated temperature, such that a solution which is saturated or nearly saturated with 5,11-dihydro-11-ethyl-5-methyl-8-{2-{(1-oxido-4-quinolinyl)oxy}ethyl}-6H-dipyrido[3,2-b:2',3'-e][1,4]diazepin-6-one is obtained. This solution is then allowed to cool slowly to a lower temperature, until a crystalline precipitate is first observed, or optionally seed crystals of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one Anhydrous Form III (if available) may be added to the original solution. The slurry is then held at this temperature until precipitation is pronounced, then either filtered or cooled further and then filtered. The solid is then dried until all surface solvents have been removed, providing 5,11-dihydro-11-ethyl-5-methyl-8-{2-{(1-oxido-4-quinolinyl)oxy}ethyl}-6H-dipyrido[3,2-b:2',3'-e][1,4]diazepin-6-one Anhydrous Form III.

(B) Examples of Specific Syntheses According to the Invention

Specific syntheses of the two crystalline forms of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one that are in accordance with the invention are described in the following examples.

EXAMPLE 1

Preparation of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one dihydrate 29.1 Kg of crude 5,11-dihydro-11-ethyl-5-methyl-8-{2-{(1-oxido-4-quinolinyl)oxy}ethyl}-6H-dipyrido[3,2-b:2',3'-e][1,4]diazepin-6-one as a wet cake was charged to an inerted 400 L reactor. The reactor was again inerted, then 105 Kg MeCN and 8.3 Kg 0.002M HCl were charged, and the mixture heated to 70° C. in the dark and held there for 30 minutes. The solution was then cooled to 22° C. over 1 hour, held one hour, and the slurry thus obtained was centrifuged, washing the cake with 35 Kg of 8:1 MeCN:$H_2O$. The recrystallized 5,11-dihydro-11-ethyl-5-methyl-8-{2-{(1-oxido-4-quinolinyl)oxy}ethyl}-6H-dipyrido[3,2-b:2',3'-e][1,4]diazepin-6-one wet cake (18.55 Kg) was then packed out and again returned to the reactor. The reactor was inerted, then 12.6 Kg $H_2O$ and 77.7 Kg EtOH (SDA-2B) were charged, and the mixture heated to 70° C. in the dark. Once in solution, the mixture was transferred hot into a second reactor through an in line polishing filter, using 22.1 Kg of 8:1 EtOH:$H_2O$ to aid the transfer and wash out the first reactor. About 22 L of solvent was then removed by atmospheric pressure distillation. To the resulting solution was then added 300 g of 6N HCl to protonate the impurity (~2%) of ether 5,11-dihydro-11-ethyl-5-methyl-8-{2-{(4-quinolinyl)oxy}ethyl}-6H-dipyrido[3,2-b:2',3'-e] [1,4]diazepin-6-one. The solution was then cooled to 50° C. over 1 hour and seeded with 100 g of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one dihydrate. The mixture was then linearly cooled to 22° C. over 8 hours. The slurry thus obtained was then centrifuged, washing the cake with 15 Kg of 8:1 EtOH:$H_2O$. The solid was dried in the centrifuge until KF water analysis reached 7.5% to give 14.45 Kg of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate (67% overall yield from intermediate ether 5,11-dihydro-11-ethyl-5-methyl-8-{2-{(4-quinolinyl)oxy}-ethyl}-6H-dipyrido[3,2-b:2',3'-e][1,4]diazepin-6-one C1) as a colorless solid with HPLC purity of 99.1%. M.p. 199° C.; $^1$H NMR (400 MHz, CDCl3)δ: 8.69 (d, J=7.0 Hz, 1H), 8.62 (d, J=8.7 Hz, 1H), 8.39 (d, J=2.4 Hz, 1H), 8.21 (d, J=8.4 Hz, 1H), 8.18 (dd, J=4.7, 1.6 Hz, 1H), 7.8 (dd, J=5.4, 5.4 Hz, 1H), 7.70 (dd, J=7.2, 7.2 Hz, 1H), 7.47 (dd, J=8.0, 1.6 Hz, 1H), 7.07 (dd, J=7.9, 4.7 Hz, 1H), 6.78 (d, J=7.0 Hz, 1H), 4.42 (dd, J=6.2, 6.2 Hz, 2H), 4.18 (q, J=6.9 Hz, 2H), 3.50 (s, 3H), 3.22 (dd, J=6.2, 6.2 Hz, 2H), 1.24 (t, J=7.0 Hz, 3H). $^{13}$C NMR (125 MHz, d6-DMSO)δ: 166.25 (C6), 157.68 (C15), 153.95 (C12), 151.31 (C21), 151.13 (C9), 144.02 (C2), 141.21 (C7), 140.47 (C30), 135.36 (C23), 131.70 (C4), 131.11 (C13), 130.58 (C26), 128.86 (C8), 128.02 (C27), 122.28 (C28), 122.07 (C29), 120.24 (C3+C14), 119.24 (C25), 101.92 (C22), 68.87 (C20), 40.36 (C17), 36.71 (C16), 30.59 (C19), 13.40 (C18). Anal. Calcd for $C_{25}H_{27}N_5O_5$: C, 62.88; H, 5.70; N, 14.67. Found C, 62.86; H, 5.72; N, 14.54.

EXAMPLE 2

Preparation of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one Anhydrous Form III 22.5 Kg of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one dihydrate was dried in a vacuum oven (40° C./44 mm) to constant weight, requiring about 60 hours, and furnishing 20.4 Kg (98% recovery) of anhydrous 5,11-dihydro-11-ethyl-5-methyl-8-{2-{(1-oxido-4-quinolinyl)oxy}ethyl}-6H-dipyrido[3,2-b:2',3'-e][1,4]diazepin-6-one. This solid was then charged into an inerted 200 L reactor protected from light. 82 liters anhydrous ethanol was then added, and the resultant slurry heated to reflux. Additional anhydrous ethanol (10 L) was then added to give a clear solution. This solution was then linearly cooled to 67° C. over one hour, and then seeded with 205 g 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III added subsurface as a slurry in 2 liters absolute ethanol. The batch was then cooled linearly to 35° C. over 4 hours, and then cooled linearly to 30° C. over 12 hours. The batch was then cooled to 10° C. over one hour, giving a slurry. This mixture was then vacuum distilled (30° C./400 mm), collecting 32 liters of ethanol. The resultant slurry was then cooled to 10° C. over one hour, and then filtered, washing the cake with 6 liters ethanol. The solid was then dried (42° C./51 mm) for 20 hours to give 19.2 Kg (94%) of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III as an off-white solid.

EXAMPLE 3

Manufacture of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one dihydrate An inerted 400 L reactor was charged with 11.2 Kg of 5,11-dihydro-11-ethyl-5-methyl-8-{2-{(4-quinolinyl)oxy}ethyl}-6H-dipyrido[3,2-b:2',3'-e][1,4]diazepin-6-one HCl (24.0 mol, 1 eq.) and 9.9 Kg $Na_3PO_4$ (60.0 mol, 2.5 eq.), and the reactor was reinerted. 3.75 Kg MeOH and 53.7 Kg $CH_2Cl_2$ were then charged, followed by 125 Kg $H_2O$. The mixture was agitated at 100 rpm for 15 minutes at 22° C., then 34.5 Kg 32% peracetic acid/HOAc (146 mol, 6.1 eq.) was charged over 10 minutes. The resulting mixture was agitated well in the dark for 2.5 hours at 22° C., and then cooled to 5° C. To this cold mixture was then slowly added 91.9 Kg 2M $Na_2S_2O_3$ over 45 minutes, maintaining the internal temperature below 15° C. The mixture was then stirred at 22° C. for 1 hour, and then the organic solvents were removed by distillation at 45° C./50 mm, collecting 31 L of distillate. The contents were then stirred 4 hours at 22° C. and the resultant slurry was centrifuged, and the resultant cake was washed with 75 Kg $H_2O$. The resulting wet cake (15.5 Kg) was then packed out and returned to the reactor. An additional 13.6 Kg of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one wet cake from a different batch was then charged into the reactor, for a total of 29.1 Kg wet cake.

The reactor was inerted, then 105 Kg MeCN and 8.3 Kg 0.002M HCl were charged into the reactor, and the mixture was heated to 70° C. in the dark and held there for 30 minutes. The solution was then cooled to 22° C. over 1 hour, held at this temperature for one hour, and the slurry thus obtained was centrifuged, washing the cake with 35 Kg of 8:1 MeCN:$H_2O$. The recrystallized 5,11-dihydro-11-ethyl-5-methyl-8-{2-{(1-oxido-4-quinolinyl)oxy}ethyl}-6H-dipyrido[3,2-b:2',3'-e][1,4]diazepin-6-one wet cake (18.55 Kg) was then packed out and again returned to the reactor. The reactor was inerted, then 12.6 Kg $H_2O$ and 77.7 Kg EtOH (SDA-2B) were charged, and the mixture heated to 70° C. in the dark. Once in solution, the mixture was transferred hot into a second reactor through an in line polishing filter, using 22.1 Kg of 8:1 EtOH:$H_2O$ to aid the transfer and wash out the first reactor. About 22 L of solvent was then removed by atmospheric pressure distillation. To the resulting solution was then added 300 g of 6N HCl to protonate the impurity (~2%) of ether 5,11-dihydro-11-ethyl-5-methyl-8-{2-{(4-quinolinyl)oxy}ethyl}-6H-dipyrido[3,2-b:2',3'-e] [1,4]diazepin-6-one. The solution was then cooled to 50° C. over 1 hour and seeded with 100 g of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one.2 $H_2O$. The mixture was then linearly cooled to 22° C. over 8 hours. The slurry thus obtained was centrifuged, washing the cake with 15 Kg of 8:1 EtOH:$H_2O$. The solid was dried in the centrifuge until KF water analysis reached 7.5% to give 14.45 Kg of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate (67% overall yield from 5,11-dihydro-11-ethyl-5-methyl-8-{2-{(4-quinolinyl)oxy}ethyl}-6H-dipyrido[3,2-b:2',3'-e] [1,4]diazepin-6-one C1) as a colorless solid with HPLC purity of 99.1%. M.p. 199° C.; $^1$H NMR (400 MHz, CDCl3) δ: 8.69 (d, J=7.0 Hz, 1H), 8.62 (d, J=8.7 Hz, 1H), 8.39 (d, J=2.4 Hz, 1H), 8.21 (d, J=8.4 Hz, 1H), 8.18 (dd, J=4.7, 1.6 Hz, 1H), 7.8 (dd, J=5.4, 5.4 Hz, 1H), 7.70 (dd, J=7.2, 7.2 Hz, 1H), 7.47 (dd, J=8.0, 1.6 Hz, 1H), 7.07 (dd, J=7.9, 4.7 Hz, 1H), 6.78 (d, J=7.0 Hz, 1H), 4.42 (dd, J=6.2, 6.2 Hz, 2H), 4.18 (q, J=6.9 Hz, 2H), 3.50 (s, 3H), 3.22 (dd, J=6.2, 6.2 Hz, 2H), 1.24 (t, J=7.0 Hz, 3H). $^{13}$C NMR (125 MHz, d6-DMSO) δ: 166.25 (C6), 157.68 (C5), 153.95 (C12), 151.31 (C21), 151.13 (C9), 144.02 (C2), 141.21 (C7), 140.47 (C30), 135.36 (C23), 131.70 (C4), 131.11 (C13), 130.58 (C26), 128.86 (C8), 128.02 (C27), 122.28 (C28), 122.07 (C29), 120.24 (C3+C14), 119.24 (C25), 101.92 (C22), 68.87 (C20), 40.36 (C17), 36.71 (C16), 30.59 (C19), 13.40 (C18). Anal. Calcd for $C_{25}H_{27}N_5O_5$: C, 62.88; H, 5.70; N, 14.67. Found C, 62.86; H, 5.72; N, 14.54.

EXAMPLE 4

Laboratory Synthesis of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one anhydrous Form III.

2.05 g of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate was dried in a vacuum oven at 85° C. to constant weight. The resulting solid was then recrystallized from 8 mL absolute ethanol at 70° C., and allowed to cool slowly to ambient temperature over 18 h. The resulting slurry was then filtered and washed with a small amount of absolute ethanol, air-dried briefly, then dried under a nitrogen sweep to constant weight, 1.67 g (88%). XRPD showed the sample to be 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III.

EXAMPLE 5

Manufacture of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III 22 Kg of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate (46.1 mol, 1 eq.) was placed in a tray drier and dried at 40 mm vacuum and 60° C. until KF water analysis showed $H_2O$ content <0.2% (48 hours). The solid (19.5 Kg) was then charged to an inerted 200 L reactor, which was then reinerted. 80 L absolute ethanol (SDA-2B) was then charged, and the mixture was agitated at 100 rpm as the temperature was raised to 82° C. Withdrawal of a reactor aliquot showed a clear solution. The mixture was then cooled to 72° C. and seeded subsurface with 200 g 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III as an ethanol slurry. The reactor contents were then linearly cooled to ambient temperature over 18 h, then cooled further to 14° C. and held at this temperature for one hour, then filtered. The resultant cake was then dried to constant weight in a vacuum oven at 60° C. for 24 h to give 19.2 Kg 5,11-dihydro-11-ethyl-5-methyl-8-{2-{(1-oxido-4-quinolinyl)oxy}ethyl}-6H-dipyrido[3,2-b:2',3'-e][1,4]diazepin-6-one anhydrous Form III (95%) as an off-white solid. Analysis of the material by XRPD and comparison to an authentic standard showed it to be the 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one anhydrous Form III polymorph. The HPLC purity was found to be 99.2%. M.p. 198.2° C.; $^1$H NMR (400 MHz, CDCl3) δ: 8.69 (d, J=7.0 Hz, 1H), 8.62 (d, J=8.7 Hz, 1H), 8.39 (d, J=2.4 Hz, 1H), 8.21 (d, J=8.4 Hz, 1H), 8.18 (dd, J=4.7, 1.6 Hz, 1H), 7.8 (dd, J=5.4, 5.4 Hz, 1H), 7.70 (dd, J=7.2, 7.2 Hz, 1H), 7.47 (dd, J=8.0, 1.6 Hz, 1H), 7.07 (dd, J=7.9, 4.7 Hz, 1H), 6.78 (d, J=7.0 Hz, 1H), 4.42 (dd, J=6.2, 6.2 Hz, 2H), 4.18 (q, J=6.9 Hz, 2H), 3.50 (s, 3H), 3.22 (dd, J=6.2, 6.2 Hz, 2H), 1.24 (t, J=7.0 Hz, 3H). $^{13}$C NMR (125 MHz, d6-DMSO) δ: 166.25 (C6), 157.68 (C15), 153.95 (C12), 151.31 (C21), 151.13 (C9), 144.02 (C2), 141.21 (C7), 140.47 (C30), 135.36 (C23), 131.70 (C4), 131.11 (C13), 130.58 (C26), 128.86 (C8), 128.02 (C27), 122.28 (C28), 122.07 (C29), 120.24 (C3+C14), 119.24 (C25), 101.92 (C22), 68.87 (C20), 40.36 (C17), 36.71 (C16), 30.59 (C19), 13.40 (C18). Anal. Calcd for $C_{25}H_{23}N_5O_3$: C, 62.92; H, 5.30; N, 15.77. Found C, 62.76; H, 4.97; N, 15.72.

3. X-ray Powder Diffraction Methodology

Any high quality X-Ray powder diffractometer may employed for the purpose of distinguishing between various crystalline forms of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one.

Exemplary XRPD patterns of the dihydrate and anhydrous Form III crystalline forms in accordance with the invention were produced using a Bruker AXS X-Ray Powder Diffractometer, Model D8 Advance. The instrument is equipped with a long fine focus x-ray tube. The tube power was set to 40 kV and 40 mA. The instrument was operated in parafocusing mode using a 1.0 mm divergence slit, 1.0 mm antiscatter slit, 0.2 mm detector slit, 0.6 mm monochromer slit, graphite monochromator and a NaI scintillation detector. Step scans were run from 2 to 35°2θ, at 0.05° per step, 4 sec per step. A reference quartz standard was used to check instrument alignment. Samples were prepared for analysis by filling a zero background silicon holder. The resulting XRPD patterns are reproduced in FIGS. 1 and 3.

4. Additional Methods for Characterization

The crystalline forms in accordance with the invention may, optionally, be further characterized by differential scanning calorimetry (DSC). DSC thermal curves for the dihydrate and anhydrous Form III crystalline forms in accordance with the invention are shown in FIGS. 2 and 4, respectively.

A further means of characterization is thermomicroscopy. The dihydrate exhibits the following thermal events when observed by thermomicroscopy (heating rate=10° C./min) using a polarized light microscope:

1. Crystal clouding and evolution of volatiles indicative of dehydration in the range of ~75-112° C., resulting in a dehydrated phase.
2. Melting of the dehydrated phase in the range of ~155-162° C.
3. Re-crystallization in the range of ~162-188° C.
4. Final melt in the range of ~195-203° C.

Moreover, it may be confirmed that the dihydrate is a stoichiometric dihydrate by thermogravimetry/Fourier transform infrared spectrographic analysis (TGA/FTIR) or similar techniques.

5. Thermodynamic Preferences for Dihydrate and Anhydrous Form III

Solubility experiments were used to determine the unique phase diagram shown in FIG. 5 for the various forms of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one. The phase diagram indicates that anhydrous Form III is thermodynamically preferred over anhydrous Form I at 25° C. Additionally, anhydrous Form III is thermodynamically favored over the dihydrate and anhydrous Form I at 25° C. when in contact with ethanol solutions containing<~2.7±0.5 wt % water. Conversely, the dihydrate is thermodynamically preferred over anhydrous Form I and Form III when in contact with ethanol solutions containing >~2.7 wt % water and saturated with 5,11-dihydro-11-ethyl-5-methyl-8-{2-{(1-oxido-4-quinolinyl)oxy}ethyl}-6H-dipyrido[3,2-b:2',3'-e][1,4]diazepin-6-one.

6. Utility

The dihydrate and anhydrous Form III of 5,11-dihydro-11-ethyl-5-methyl-8-{2-{(1-oxido-4-quinolinyl)oxy}ethyl}-6H-dipyrido[3,2-b:2',3'-e][1,4]diazepin-6-one that are in accordance with the invention may be used to treat HIV infection in humans, in the manner described in U.S. Pat. No. 6,420,359 and the corresponding WO0196338. The compound, in either of these two crystalline forms, may be incorporated into pharmaceutical formulations and administered in accordance with the dosing regimens described in U.S. Pat. No. 6,420,359 and the corresponding WO0196338.

What is claimed is:

1. The crystalline form of 5,11-dihydro-11-ethyl-5-methyl-8-{2-{(1-oxido-4-quinolinyl)oxy}ethyl}-6H-dipyrido [3,2-b:2',3'-e] [1,4]diazepin-6-one dihydrate having an X-ray powder diffraction pattern that comprises peaks at 23.4, 24.9, 17.3, 24.3, 12.1, 18.5 and 17.6 degrees 2θ (±0.2 degrees 2θ) and wherein said X-ray powder diffraction pattern is made using $CuK_\alpha$ radiation.

2. 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one wherein at least 50% of said substance is present in the form of the crystalline dihydrate in accordance with claim 1.

3. A pharmaceutical formulation comprising the crystalline substance of claim 1, and a pharmaceutically acceptable carrier or diluent.

4. The crystalline Form III of anhydrous 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one having an X-ray powder diffraction pattern that comprises peaks at 11.6, 22.5, 8.3, 12.0, 12.4, 5.8 and 20.8 degrees 2θ(±0.2 degrees 2θ) and wherein said X-ray powder diffraction pattern is made using $CuK_\alpha$ radiation.

5. 5,11-Dihydro-11-ethyl-5-methyl-8-{2-{(1-oxido-4-quinolinyl)oxy}ethyl}-6H-dipyrido[3,2-b:2',3'-e] [1,4]diazepin-6-one wherein at least 50% of said substance is present as the crystalline anhydrous Form III in accordance with claim 4.

6. A pharmaceutical formulation comprising the crystalline substance of claim 4, and a pharmaceutically acceptable carrier or diluent.

7. A method for making the crystalline form of 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate in accordance with claim 1, said method comprising the following steps:

(a) dissolving 5,11-dihydro-11-ethyl-5-methyl-8-{2-{(1-oxido-4-quinolinyl)oxy}ethyl}-6H-dipyrido[3,2-b:2', 3'-e] [1,4]diazepin-6-one in a mixture of $H_2O$ and a water-miscible solvent, to form a saturated or nearly saturated solution, with the proviso that the amount of $H_2O$ must be at least the quantity required to form a stoichiometric dihydrate;

(b) cooling the solution to precipitate 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate out of solution;

(c) removing the precipitate from the solution; and (d) drying the solid until all surface solvents have been removed.

8. A method for making the anhydrous Form III crystalline form of 5,11-dihydro-11-ethyl-5-methyl-8-{2-{(1-oxido-4-quinolinyl)oxy}ethyl}-6dipyrido[3,2-b:2',3'-e]

[1,4]diazepin-6-one in accordance with claim 4, which method comprises the following steps:
 (a) drying 5,11-dihydro-11-ethyl-5-methyl-8-{2-{(1-oxido-4-quinolinyl)oxy}ethyl}-6H-dipyrido[3,2-b:2',3'-e] [1,4]diazepin-6-one dihydrate or trihydrate to remove water and produce an anhydrous material;
 (b) dissolving the anhydrous solid in an anhydrous solvent, to produce a saturated or nearly saturated solution;
 (c) cooling the solution to precipitate out anhydrous Form III crystalline form of 5,11-dihydro-11-ethyl-5-methyl-8-{2-{(1-oxido-4-quinolinyl)oxy}ethyl}-6H-dipyrido [3,2-b:2',3'-e] [1,4]diazepin-6-one;
 (d) separating the precipitate from the solution; and
 (e) drying the solid until all surface solvents have been removed.

* * * * *